United States Patent
Merchant et al.

(10) Patent No.: US 8,102,528 B2
(45) Date of Patent: Jan. 24, 2012

(54) PARTICLE STANDARD AND METHOD OF CALIBRATING OR VALIDATING AN OPTICAL PARTICLE ANALYZER

(75) Inventors: Clark Adrien Merchant, Kanata (CA); Peter Oma, Ottawa (CA)

(73) Assignee: Brightwell Technologies Inc., Ottawa (CA)

(*) Notice: Subject to any disclaimer, the term of this patent is extended or adjusted under 35 U.S.C. 154(b) by 333 days.

(21) Appl. No.: 12/549,781

(22) Filed: Aug. 28, 2009

(65) Prior Publication Data

US 2009/0308133 A1   Dec. 17, 2009

Related U.S. Application Data

(63) Continuation-in-part of application No. 12/209,260, filed on Sep. 12, 2008, now Pat. No. 7,859,664.

(60) Provisional application No. 60/971,935, filed on Sep. 13, 2007.

(51) Int. Cl.
*G01J 1/00* (2006.01)
*G01N 15/02* (2006.01)
*G01N 37/00* (2006.01)

(52) U.S. Cl. ..... 356/336; 356/335; 356/337; 356/243.1; 356/243.2; 73/1.03

(58) Field of Classification Search .... 356/243.1–243.8, 356/335–340, 246; 73/1.03, 28.02, 864.71
See application file for complete search history.

(56) References Cited

U.S. PATENT DOCUMENTS

| | | | |
|---|---|---|---|
| 4,331,862 A | 5/1982 | Ryan | 337/29 |
| 4,704,891 A | 11/1987 | Recktenwald et al. | 250/252.1 |
| 5,728,582 A | 3/1998 | Taki et al. | 436/10 |
| 5,747,667 A | 5/1998 | Sadar | 73/1.02 |
| 5,835,211 A * | 11/1998 | Wells et al. | 356/336 |
| 6,074,879 A | 6/2000 | Zelmanovic et al. | 436/10 |
| 6,542,833 B1 | 4/2003 | Nygaard | 702/46 |
| 6,784,981 B1 * | 8/2004 | Roche et al. | 356/39 |
| 6,807,874 B2 * | 10/2004 | Totoki | 73/864.71 |
| 7,057,198 B2 * | 6/2006 | Meinhart et al. | 250/573 |
| 7,187,441 B1 * | 3/2007 | Sevick-Muraca et al. | 356/336 |
| 7,605,919 B2 * | 10/2009 | Oma et al. | 356/339 |
| 7,859,664 B2 * | 12/2010 | Oma et al. | 356/335 |
| 2009/0073437 A1 | 3/2009 | Oma et al. | 356/335 |

* cited by examiner

*Primary Examiner* — Sang Nguyen
(74) *Attorney, Agent, or Firm* — Teitelbaum & MacLean; Neil Teitelbaum; Doug MacLean

(57) ABSTRACT

The present invention provides a particle standard including particles having optical properties similar to those of a carrier in which the particles are dispersed, as well as a method of calibrating or validating a subject optical particle analyzer with respect to a reference optical particle analyzer by using the particle standard. In the method, the particle standard is analyzed with the reference optical particle analyzer to obtain a reference particle concentration and a reference particle-size distribution. Analogously, the particle standard is analyzed with the subject optical particle analyzer to obtain a subject particle concentration and a subject particle-size distribution. The subject particle concentration and the subject particle-size distribution are then compared to the reference particle concentration and the reference particle-size distribution, respectively, and the subject optical particle analyzer is adjusted accordingly.

3 Claims, 2 Drawing Sheets

PARTICLE STANDARD AND METHOD OF CALIBRATING OR VALIDATING AN OPTICAL PARTICLE ANALYZER

CROSS-REFERENCE TO RELATED APPLICATIONS

This application is a continuation-in-part of U.S. patent application Ser. No. 12/209,260 filed Sep. 12, 2008 now U.S. Pat. No. 7,859,664, which claims priority from U.S. Provisional Application Ser. No. 60/971,935, filed Sep. 13, 2007, both which are incorporated herein by reference.

TECHNICAL FIELD OF THE INVENTION

The present invention relates to particle standards for calibrating or validating optical particle analyzers and to methods of calibrating or validating optical particle analyzers.

BACKGROUND OF THE INVENTION

In the pharmaceutical industry, an optical particle analyzer is frequently used to analyze samples including particles of biological material dispersed in a water-based carrier. As the optical properties of the particles in such samples are similar to those of the carrier, the analysis of such samples is particularly challenging. Not all of the particles in such samples may be detectable by the optical particle analyzer, owing to detection-sensitivity limitations. To achieve reliable and repeatable results for the analysis, the optical particle analyzer must be properly calibrated and periodically validated by using a particle standard that optically approximates such samples. In particular, it is highly desirable that the fraction of particles detected in such samples is substantially the same when the samples are analyzed at different times or locations, with the same or different optical particle analyzers.

Unfortunately, samples including particles of biological material dispersed in a water-based carrier are, generally, unstable and cannot be practically used as particle standards. Therefore, a particle standard that may serve as a stable optical surrogate for such samples and a method of calibrating or validating an optical particle analyzer by using the particle standard are required.

However, most conventional methods of calibrating or validating an optical particle analyzer involve the use of a particle standard including particles having optical properties dissimilar to those of a carrier in which the particles are dispersed. For example, methods involving the use of a particle standard including polymer particles having a refractive index significantly different from that of a water-based carrier in which the particles are dispersed are described in U.S. Pat. No. 5,728,582 to Taki, et al., issued on Mar. 17, 1998, in U.S. Pat. No. 4,704,891 to Recktenwald, et al., issued on Nov. 10, 1987, and in U.S. Pat. No. 4,331,862 to Ryan, issued on May 25, 1982, which are incorporated herein by reference. For another example, methods involving the use of a particle standard including stained particles having fluorescence or transmission properties significantly different from those of an unstained carrier in which the particles are dispersed are described in U.S. Pat. No. 6,542,833 to Nygaard, issued on Apr. 1, 2003, which is incorporated herein by reference, in U.S. Pat. No. 5,728,582, and in U.S. Pat. No. 4,704,891.

As the particles in the particle standards used in such methods are easily detected by the optical particle analyzer, the particle standards do not challenge the detection sensitivity of the optical particle analyzer. Optical particle analyzers having different detection sensitivities are, typically, able to detect substantially all of the particles in the particle standards; however, they may detect significantly different fractions of particles in samples including particles of biological material dispersed in a water-based carrier, leading to unreliable and unrepeatable results for the analysis of such samples.

Furthermore, most conventional methods of calibrating or validating an optical particle analyzer, such as those mentioned heretofore, and those described in U.S. Pat. No. 6,074,879 to Zelmanovic, et al., issued on Jun. 13, 2000, and in U.S. Pat. No. 5,747,667 to Sadar, issued on May 5, 1998, which are incorporated herein by reference, require that substantially all of the particles in a particle standard be detected by the optical particle analyzer. Although, as mentioned heretofore, this requirement may be easy to fulfill for a particle standard including particles having optical properties dissimilar to those of a carrier in which the particles are dispersed, it may be difficult or impossible to fulfill for a particle standard that optically approximates samples including particles of biological material dispersed in a water-based carrier.

SUMMARY OF THE INVENTION

An object of the present invention is to provide a particle standard including particles having optical properties similar to those of a carrier in which the particles are dispersed, as well as a method of calibrating or validating a subject optical particle analyzer with respect to a reference optical particle analyzer by using the particle standard.

Accordingly, the present invention relates to a particle standard for calibrating or validating a subject optical particle analyzer with respect to a reference optical particle analyzer, comprising: a carrier; and particles dispersed in the carrier, wherein the particles have particle sizes within a reference particle-size range of the reference optical particle analyzer, and wherein the particles have optical properties similar to those of the carrier, such that less than substantially all of the particles are detectable by the reference optical particle analyzer.

Another aspect of the present invention relates to a method of calibrating or validating a subject optical particle analyzer with respect to a reference optical particle analyzer, comprising: providing a particle standard comprising: a carrier; and particles dispersed in the carrier, wherein the particles have particle sizes within a reference particle-size range of the reference optical particle analyzer, and wherein the particles have optical properties similar to those of the carrier, such that less than substantially all of the particles are detectable by the reference optical particle analyzer; analyzing the particle standard with the reference optical particle analyzer to obtain a reference particle concentration and a reference particle-size distribution; analyzing the particle standard with the subject optical particle analyzer to obtain a subject particle concentration and a subject particle-size distribution; comparing the subject particle concentration to the reference particle concentration and the subject particle-size distribution to the reference particle-size distribution to determine a first difference and a second difference, respectively; and adjusting the subject optical particle analyzer on the basis of the first difference and the second difference.

BRIEF DESCRIPTION OF THE DRAWINGS

The present invention will be described in greater detail with reference to the accompanying drawings, which relate to exemplary, preferred embodiments thereof, wherein.

DETAILED DESCRIPTION OF THE INVENTION

Figure 1:
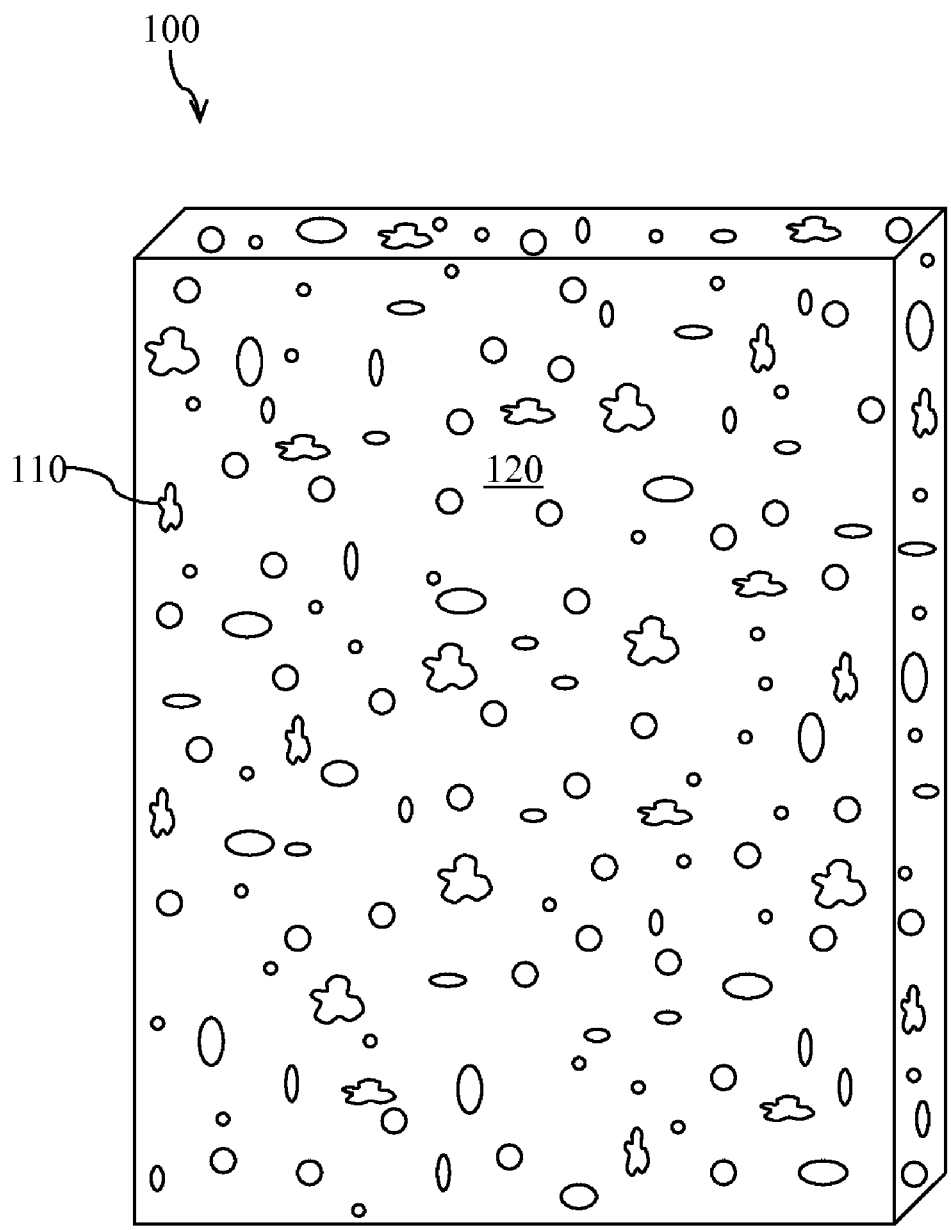
FIG. 1 is a schematic illustration of an oblique view of a particle standard according to the present invention.

With reference to FIG. 1, the present invention provides a particle standard 100 for calibrating or validating a subject optical particle analyzer with respect to a reference optical particle analyzer.

The subject optical particle analyzer and the reference optical particle analyzer may be any type of instrument that employs light having a wavelength between about 200 nm and 1000 nm to analyze particles, such as a micro-flow imaging (MFI) particle analyzer, a light-obscuration particle analyzer, or a light-scattering particle analyzer. Although the subject optical particle analyzer and the reference optical particle analyzer may be different types of instrument, to achieve maximum reliability and repeatability, it is preferred that the subject optical particle analyzer and the reference optical particle analyzer be the same type of instrument. For example, in a preferred embodiment, the subject optical particle analyzer and the reference optical particle are both MFI particle analyzers. Ideally, the subject optical particle analyzer and the reference optical particle analyzer are substantially identical and have the same instrument specifications.

The reference optical particle analyzer serves as a "gold standard" instrument, in terms of detection sensitivity, against which the subject optical particle analyzer is compared during calibration or validation of the subject optical particle analyzer. The particle standard 100 provides an advantageous means for comparing the subject optical particle analyzer to the reference optical particle analyzer.

For example, during calibration in manufacture, a particle standard 100 prepared on-site at the manufacturer's facilities may be used to compare a subject optical particle analyzer manufactured on-site to a reference optical particle analyzer housed on-site. For another example, a particle standard 100 prepared on-site at the manufacturer's facilities may be used to compare a subject optical particle analyzer located off-site to a reference optical particle analyzer housed on-site, during validation or recalibration in the field. Once calibrated or validated in such a manner, any optical particle analyzer can itself serve as a reference optical particle analyzer.

The particle standard 100 includes particles 110 dispersed in a carrier 120. The particles 110 have particle sizes within a reference particle-size range of the reference optical particle analyzer. The particle sizes are also within a subject particle-size range of the subject optical particle analyzer, which is, preferably, equivalent to the reference particle-size range.

The particles 110 are, typically, polydisperse in particle shape, having a variety of particle shapes. As the particle shapes are, usually, irregular, they are determined by measuring the particle equivalent circular diameter (ECD), the particle Feret diameter, the particle Feret length, the particle Feret width, the particle aspect ratio, the particle circularity, the particle absorption intensity, or any other particle dimension measurable by conventional particle-morphology algorithms. Preferably, the particles 110 are agglomerates of primary particles. More preferably, the particles 110 are porous agglomerates.

The particles 110 are also, typically, polydisperse in particle size, having a variety of particle sizes. Preferably, the particle sizes are distributed over a range including at least a lower part of the reference particle-size range. More preferably, the particle sizes are distributed over a range extending below the reference particle-size range, as well. Depending on the reference particle-size range, the particle sizes are, typically, between about 0.1 µm and 1 mm. For example, for calibrating or validating a subject optical particle analyzer having a subject particle-size range of 1 µm to 70 µm with respect to a reference optical particle analyzer having a reference particle-size range of 1 µm to 70 µm, a particle standard 100 including particles 110 having particle sizes distributed over a range of about 0.5 µm to 10 µm may be suitable.

The particles 110 are dispersed in the carrier 120 at a particle concentration within a reference particle-concentration range of the reference optical particle analyzer. The particle concentration is also within a subject particle-concentration range of the subject optical particle analyzer, which is, preferably, equivalent to the reference particle-concentration range. Typically, the particle concentration is between about 1000 particles/mL and 10 000 000 particles/mL; however, the particle concentration may also be lower than 1000 particles/mL.

In most instances, the particle standard 100 has a particle-size distribution that is substantially exponential, with particle concentration per particle-size interval increasing rapidly with decreasing particle-size interval.

It should be noted that it is not necessary for characteristics such as the particle concentration and the particle-size distribution to be known exactly, as the particle standard 100 is intended as a relative standard for comparing the subject optical particle analyzer against the reference optical particle analyzer. Rather, the particle standard 100 is, typically, associated with a record of a reference particle concentration and a reference particle-size distribution obtained by analyzing the particle standard 100 with the reference optical particle analyzer. This advantageous feature distinguishes the particle standard 100 of the present invention from most conventional particle standards, which are absolute standards with defined characteristics.

However, if desired, characteristics such as the particle concentration and the particle-size distribution may be determined by analyzing the particle standard 100 with a non-optical particle analyzer, such as a Coulter counter, which is able to detect substantially all of the particles 110 in the particle standard 100. The particle concentration and the particle-size distribution determined in such a manner may then be compared and/or related to the reference particle concentration and the reference particle-size distribution.

Another advantageous feature of the particle standard 100 is that the particles 110 have optical properties, such as refractive index, transmission properties, and fluorescence properties, similar to those of the carrier 120, which allows the particle standard 100 to serve as a detection-sensitivity challenge. Preferably, the particles 110 and the carrier 120 are transparent or near-transparent.

The particles 110 and the carrier 120 have optical properties sufficiently similar that less than substantially all of the particles 110 are detectable by the reference optical particle analyzer, owing to detection-sensitivity limitations. Likewise, less than substantially all of the particles 110 are detectable by the subject optical particle analyzer. Preferably, less than 95% of the particles 110 are detectable by the reference optical particle analyzer.

It is known that less than substantially all of the particles 110 are detectable by the reference optical particle analyzer because adjustment of the reference optical particle analyzer to increase or decrease its detection sensitivity allows it to detect a larger or smaller fraction of particles 110. If desired, the fraction of particles 110 detectable by the reference optical particle analyzer may be determined by comparing the reference particle concentration, which is lower than an actual particle concentration of the particle standard 100, to the particle concentration determined by using a non-optical particle analyzer, which substantially corresponds to the actual particle concentration. Preferably, the reference optical particle analyzer is adjusted to a detection sensitivity that is near the highest attainable by the reference optical particle analyzer, but which is also attainable by the subject optical particle analyzer upon calibration or validation.

As the reference optical particle analyzer and the subject optical particle analyzer, prior to calibration or validation, have different detection sensitivities, different fractions of particles 110 are detectable by each optical particle analyzer. Advantageously, by means of the particle standard 100, the detection sensitivity of the subject optical particle analyzer may be standardized with that of the reference optical particle analyzer, such that the fraction of particles 110 detected by each optical particle analyzer is substantially the same.

Ideally, the particles 110 and the carrier 120 have optical properties similar to those of particles and carriers, respectively, encountered in samples under study for a particular application.

The particles 110 and the carrier 120 may be composed of a variety of materials, which are selected to ensure that the particle standard 100 has the features and characteristics detailed heretofore. Furthermore, the materials are selected to ensure that a dispersion of the particles 110 in the carrier 120 is sufficiently stable or has a known decay rate for a time period over which the particle standard 100 will be used. The material selected for the particles 110 must be inert and dispersible in the carrier 120. Likewise, the material selected for the carrier 120 must be inert towards the particles 110 and amenable to dispersion of the particles 110 therein. If necessary, a surfactant, a viscosity modifier, a buffer, a preservative, or another type of additive may be included in the material selected for the carrier 120.

Typically, the material selected for the particles 110 is an inorganic oxide, either crystalline or amorphous, in solid, glass, or gel form. Alternatively, the material selected for the particles 110 may be a liquid immiscible with a liquid selected as the material for the carrier 120, such that the particles 110 are microdroplets.

A preferred embodiment of the particle standard 100 includes particles 110 of precipitated silica dispersed in a water-based carrier 120. Advantageously, the preferred embodiment of the particle standard 100 serves as a stable optical surrogate for samples including particles of biological material dispersed in a water-based carrier.

In general, precipitated silica, an amorphous form of silica, is produced commercially by combining a solution of a metal silicate in water with a mineral acid. In such a process, polydisperse particles 110 of precipitated silica are formed, and further agglomeration into a gel is avoided. Similarly to many types of particles of biological material, the particles 110 of precipitated silica are porous agglomerates having irregular particle shapes. Typically, the particles 110 of precipitated silica have particle sizes between about 0.5 µm and 20 µm, and pore sizes between about 10 nm and 50 nm. Furthermore, the particles 110 of precipitated silica have optical properties similar to those of many types of particles of biological material, as well as to those of the water-based carrier 120.

The preferred embodiment of the particle standard 100 may be produced by combining the particles 110 of precipitated silica and the water-based carrier 120 to form a mixture and by then agitating the mixture to form a dispersion of the particles 110 in the carrier 120. Typically, the stability of the dispersion is increased by adjusting the pH of the carrier 120, by passivating container surfaces, or by other chemical means.

Figure 2:
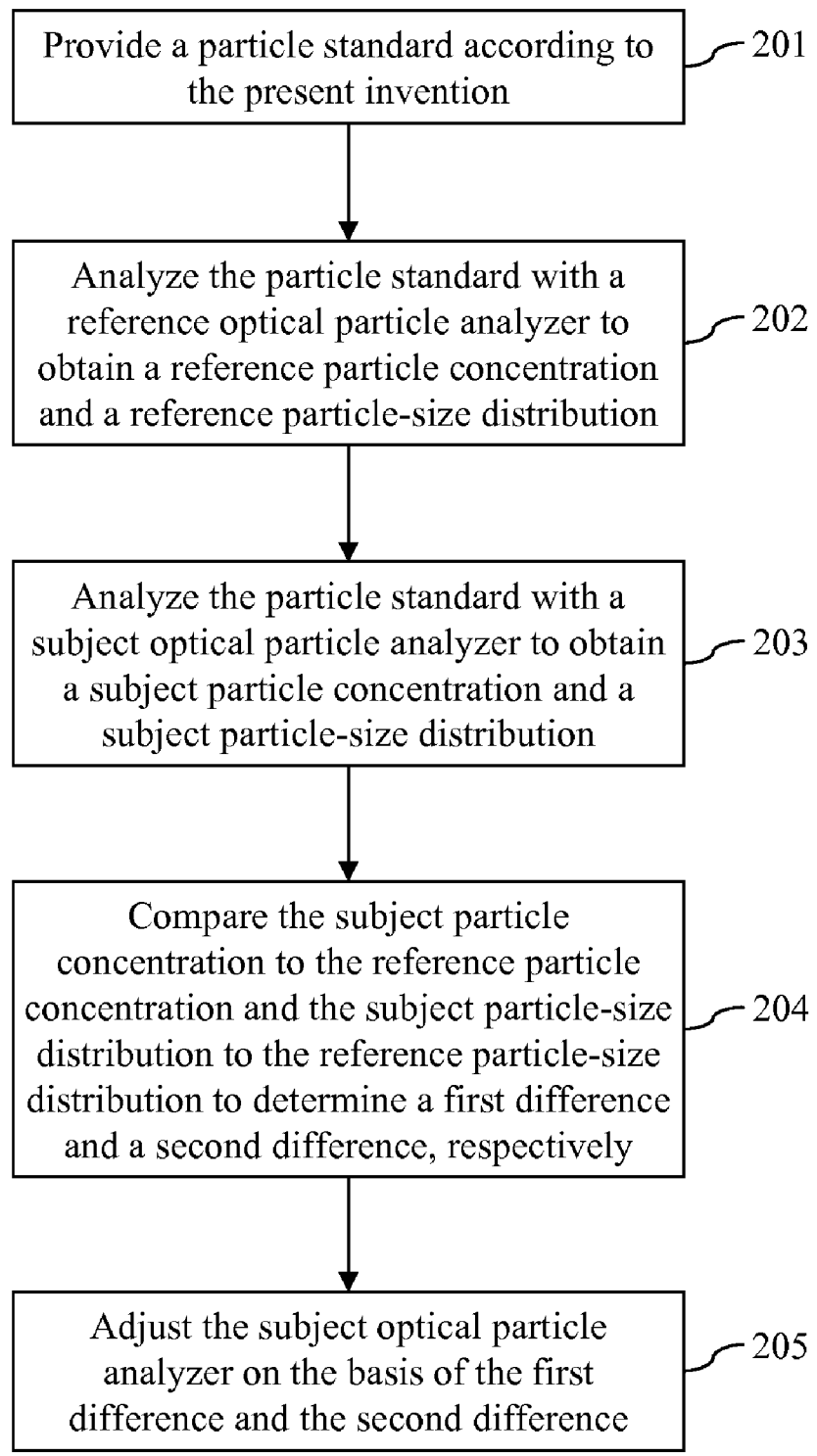
FIG. 2 is a flowchart depicting a method according to the present invention.

The present invention also provides a method of calibrating or validating the subject optical particle analyzer with respect to the reference optical particle analyzer by using the particle standard 100. With reference to FIG. 2, in a first step 201 of the method, the particle standard 100, as described heretofore, is provided. If desired, the particle standard 100 may be analyzed with a non-optical particle analyzer to determine the particle concentration and the particle-size distribution, which may then be compared and/or related to the reference particle concentration and the reference particle-size distribution, as mentioned heretofore.

In a second step 202, the particle standard 100 is analyzed with the reference optical particle analyzer, by following standard operating procedures, to obtain the reference particle concentration and the reference particle-size distribution. Typically, a record is made, in print or electronic format, of the reference particle concentration and the reference particle-size distribution, and the record is associated with the particle standard 100. The record may be stored at a site of a supplier of the particle standard 100 and/or supplied together with the particle standard 100.

Analogously, in a third step 203, the particle standard 100 is analyzed with the subject optical particle analyzer, by following standard operating procedures, to obtain a subject particle concentration and a subject particle-size distribution. In a fourth step 204, the subject particle concentration is compared to the reference particle concentration to determine a first difference, and the subject particle-size distribution is compared to the reference particle-size distribution to determine a second difference, typically, by means of the record. The subject optical particle analyzer is then adjusted on the basis of the first difference and the second difference, in a fifth step 205. For example, software, such as particle-image thresholding algorithms, and/or hardware, such as illumination components, magnification components, and detection components, of the subject optical particle analyzer may be adjusted, until the first difference and the second difference are substantially eliminated.

In some instances, the subject optical particle analyzer is first coarsely calibrated or validated by a conventional method and then finely calibrated or validated by the method of the present invention. For example, during calibration in manufacture, software and/or hardware of newly built optical particle analyzers is, usually, coarsely adjusted by using optical targets and further adjusted by using a conventional particle standard including particles having optical properties dissimilar to those of a carrier in which the particles are dispersed. However, different optical particle analyzers similarly adjusted in such a manner may, nevertheless, have different detection sensitivities for samples including particles having optical properties similar to those of a carrier in which the particles are dispersed. To standardize the detection sensitivities at a high level, software and/or hardware of the optical particle analyzers is finely adjusted by using the particle standard 100 according to the method of the present invention.

In other instances, the subject optical particle analyzer is calibrated or validated by the method of the present invention alone. For example, during validation or recalibration in the field, software and/or hardware of previously calibrated optical particle analyzers is adjusted by using the particle standard 100 according to the method of the present invention, to ensure that the optical particle analyzers maintain a high level of detection sensitivity.

Of course, numerous other embodiments of the present invention may be envisaged without departing from the spirit and scope of the invention.

We claim:

1. A method of calibrating or validating a subject optical particle analyzer with respect to a reference optical particle analyzer, comprising:
   a) providing a particle standard comprising:
      a carrier; and
      particles dispersed in the carrier, wherein the particles have particle sizes within a reference particle-size range of the reference optical particle analyzer, and wherein the particles have optical properties similar to those of the carrier, such that less than substantially all of the particles are detectable by the reference optical particle analyzer;
   b) analyzing the particle standard with the reference optical particle analyzer to obtain a reference particle concentration and a reference particle-size distribution;
   c) analyzing the particle standard with the subject optical particle analyzer to obtain a subject particle concentration and a subject particle-size distribution;
   d) comparing the subject particle concentration to the reference particle concentration and the subject particle-size distribution to the reference particle-size distribution to determine a first difference and a second difference, respectively; and
   e) adjusting the subject optical particle analyzer on the basis of the first difference and the second difference, wherein said adjusting includes adjusting software or hardware of the subject optical particle analyzer.

2. The method of claim 1, wherein b) includes making a record of the reference particle concentration and the reference particle-size distribution, and associating the record with the particle standard.

3. The method of claim 1, further comprising, prior to c), coarsely calibrating or validating the subject optical particle analyzer, wherein e) includes adjusting the subject optical particle analyzer on the basis of the first difference and the second difference to finely calibrate or validate the subject optical particle analyzer.

* * * * *